(12) United States Patent
Krishnan

(10) Patent No.: US 7,979,142 B2
(45) Date of Patent: *Jul. 12, 2011

(54) CONDUCTIVE POLYMER SHEATH ON DEFIBRILLATOR SHOCKING COILS

(75) Inventor: Mohan Krishnan, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/794,186

(22) Filed: Jun. 4, 2010

(65) Prior Publication Data

US 2010/0241209 A1    Sep. 23, 2010

Related U.S. Application Data

(63) Continuation of application No. 11/349,002, filed on Feb. 7, 2006, now Pat. No. 7,756,589, which is a continuation of application No. 09/564,741, filed on May 4, 2000, now Pat. No. 7,013,182.

(51) Int. Cl.
*A61N 1/00* (2006.01)
(52) U.S. Cl. ......................................................... 607/122
(58) Field of Classification Search .................... 607/122
See application file for complete search history.

(56) References Cited

U.S. PATENT DOCUMENTS

| | | |
|---|---|---|
| 3,815,611 A | 6/1974 | Denniston, III |
| 4,352,359 A | 10/1982 | Larimore et al. |
| 4,539,996 A | 9/1985 | Engel |
| 4,928,689 A | 5/1990 | Hauser |
| 5,090,422 A | 2/1992 | Dahl et al. |
| 5,103,837 A | 4/1992 | Weidlich et al. |
| 5,129,404 A | 7/1992 | Spehr et al. |
| 5,152,299 A | 10/1992 | Soukup |
| 5,269,810 A | 12/1993 | Hull et al. |
| 5,282,844 A | 2/1994 | Stokes et al. |
| 5,322,520 A | 6/1994 | Milder |
| 5,324,324 A | 6/1994 | Vachon et al. |
| 5,330,520 A * | 7/1994 | Maddison et al. ............ 607/122 |
| 5,385,579 A | 1/1995 | Helland |
| 5,433,730 A | 7/1995 | Alt |
| 5,476,496 A | 12/1995 | Strandberg et al. |
| 5,554,178 A | 9/1996 | Dahl et al. |
| 5,609,622 A | 3/1997 | Soukup et al. |

(Continued)

FOREIGN PATENT DOCUMENTS

WO    WO 02/13785    2/2002

(Continued)

OTHER PUBLICATIONS

International Search Report and Written Opinion issued in PCT/US2007/007558, mailed Sep. 20, 2007.

(Continued)

*Primary Examiner* — George Manuel
(74) *Attorney, Agent, or Firm* — Faegre & Benson LLP

(57) ABSTRACT

An implantable lead includes a distal portion carrying a tissue stimulating electrode, at least a portion of its outer surface being adapted to stimulate cardiac tissue, wherein the electrode is covered by a pliable, electrically conductive sheath. The sheath is made of an electrically conductive material that does not rely on porosity for electrical charge transfer. The sheath is constructed and arranged to minimize or eliminate tissue ingrowth while passing sufficient electrical energy to stimulate the tissue.

17 Claims, 4 Drawing Sheets

U.S. PATENT DOCUMENTS

| | | |
|---|---|---|
| 5,681,514 A | 10/1997 | Woody |
| 5,755,762 A | 5/1998 | Bush |
| 5,766,527 A | 6/1998 | Schildgen et al. |
| 5,837,313 A | 11/1998 | Ding et al. |
| 5,849,415 A | 12/1998 | Shalaby et al. |
| 5,853,652 A | 12/1998 | Schildgen et al. |
| 5,861,023 A | 1/1999 | Vachon |
| 5,902,329 A | 5/1999 | Hoffmann |
| 5,931,862 A | 8/1999 | Carson |
| 5,987,746 A | 11/1999 | Williams et al. |
| 5,991,667 A | 11/1999 | Feith |
| 6,117,554 A | 9/2000 | Shalaby et al. |
| 6,236,893 B1 | 5/2001 | Thong |
| 6,253,110 B1 | 6/2001 | Brabec et al. |
| 6,256,541 B1 | 7/2001 | Heil |
| 6,284,682 B1 | 9/2001 | Troczynski et al. |
| 6,361,780 B1 | 3/2002 | Ley et al. |
| 6,363,286 B1 | 3/2002 | Zhu et al. |
| 6,426,114 B1 | 7/2002 | Troczynski et al. |
| 6,709,514 B1 | 3/2004 | Hossainy |
| 6,730,324 B2 | 5/2004 | Troczynski et al. |
| 6,770,325 B2 | 8/2004 | Troczynski et al. |
| 6,889,092 B2 | 5/2005 | Zhu et al. |
| 6,896,965 B1 | 5/2005 | Hossainy |
| 7,013,182 B1 | 3/2006 | Krishnan |
| 7,115,300 B1 | 10/2006 | Hossainy |
| 7,174,221 B1 | 2/2007 | Chen et al. |
| 7,247,364 B2 | 7/2007 | Hossainy et al. |
| 7,279,175 B2 | 10/2007 | Chen et al. |
| 7,756,589 B2 | 7/2010 | Krishman |
| 7,881,808 B2 | 2/2011 | Borgaonkar et al. |
| 2002/0022826 A1 | 2/2002 | Reynolds et al. |
| 2002/0138123 A1 | 9/2002 | Casas-Bejar et al. |
| 2003/0031699 A1 | 2/2003 | Van Antwerp |
| 2003/0073961 A1 | 4/2003 | Happ |
| 2003/0093136 A1 | 5/2003 | Osypka et al. |
| 2004/0037886 A1 | 2/2004 | Hsu |
| 2004/0063805 A1 | 4/2004 | Pacetti et al. |
| 2005/0070985 A1 | 3/2005 | Knapp et al. |
| 2005/0080470 A1 | 4/2005 | Westlund et al. |
| 2005/0180919 A1 | 8/2005 | Tedeschi |
| 2006/0235499 A1 | 10/2006 | Heil, Jr. et al. |
| 2007/0051531 A1 | 3/2007 | Borgaonkar et al. |
| 2007/0128246 A1 | 6/2007 | Hossainy et al. |
| 2007/0190104 A1 | 8/2007 | Kamath et al. |
| 2008/0009939 A1 | 1/2008 | Gueriguian et al. |
| 2008/0051866 A1 | 2/2008 | Chen et al. |
| 2008/0167710 A1 | 7/2008 | Dave et al. |
| 2009/0054961 A1 | 2/2009 | Borgaonkar et al. |

FOREIGN PATENT DOCUMENTS

| | | |
|---|---|---|
| WO | WO 2005/035655 | 4/2005 |
| WO | WO 2007/030722 | 3/2007 |
| WO | WO 2007/126806 | 11/2007 |
| WO | WO 2009/051945 | 4/2009 |

OTHER PUBLICATIONS

Office Action issued in EP Application No. 07754128.2, Mailed Feb. 19, 2009, 3 pages.

Response filed Aug. 31, 2009 to Office Action dated Feb. 19, 2009, EP App 07754128.

Office Action issued in EP 07754128 mailed Mar. 31, 2010.

International Preliminary Report on Patentability, Chapter II, issued in PCT/US2006/035064, dated Sep. 12, 2007, 12 pages.

International Search Report and Written Opinion issued in PCT/US2006/035064, filed Jan. 23, 2007.

Kirby, Darren, "Use of a Bioactive Material on a Pacemaker Electrode for the Purpose of Enhancing Heart Pace/Sense Efficiency", MSC Biomedical Engineering, Thesis, Thrinty College Dublin (2003).

York, P., "New Materials and Systems for Drug Delivery and Targeting", Chemical Aspects of Drug Delivery Systems, Copyright 1996, pp. 1-10, proceedings from a symposium held Apr. 17-18, 1996 at Salford University.

* cited by examiner

CONDUCTIVE POLYMER SHEATH ON DEFIBRILLATOR SHOCKING COILS

CROSS-REFERENCE TO RELATED APPLICATION

This application is a continuation of U.S. patent application Ser. No. 11/349,002, filed on Feb. 7, 2006, which is a continuation of U.S. patent application Ser. No. 09/564,741, filed on May 4, 2000, now issued U.S. Pat. No. 7,013,182, the specifications of which are incorporated herein by reference in their entireties for all purposes.

FIELD OF INVENTION

The present invention relates generally to implantable cardiac leads and particularly to transvenous defibrillator leads having a pliable electrically conductive sheath covering the shocking coils of such leads.

BACKGROUND OF INVENTION

An automatic implantable cardioverter defibrillator (AICD) or implantable cardioverter defibrillator (ICD) detects ventricular fibrillation and delivers a series of countershocks of sufficient energy to terminate the fibrillation. Such an ICD utilizes an electrode system either attached to the outer surface of the heart by means of a large surface area patch electrode, or inserted transvenously into or near the heart. Such an ICD system may be combined with a pacemaker function.

Transvenous defibrillator leads for correcting ventricular tachycardia and ventricular fibrillation include uninsulated, helically wound shocking electrodes, formed of round wire, and rely on direct contact between the electrode and tissue or blood within or near the heart to deliver electrical energy to the heart.

When the lead is implanted, the immune system of the body responds to the implant and triggers a series of biological events. As a result of this, extensive tissue ingrowth takes place, along the length of the lead, especially around the electrode. In the case of defibrillator leads, the shocking electrode is in the form of a helically wound coil, with interstices present between the individual wires that make up the coil. Due to this exposed surface area and the high energy densities seen during shocking, the tissue ingrowth problem is exacerbated. On account of the tissue ingrowth, extensive surgical intervention may be required for lead removal.

SUMMARY OF INVENTION

The present invention provides an electrode sheath in which the passage of electrical conductivity is through a biocompatible, biostable, conductive, yet pliable material without relying on porosity and contact with body fluid.

In accordance with the present invention, there is provided an implantable cardiac lead having a distal end that includes a fixation tip and a tissue stimulating electrode, wherein the electrode is covered by a pliable, electrically conductive sheath. The fixation tip of the lead according to the present invention may include tines or a helix screw for providing fixation. It is known that the fibrosis at the site of the fixation tip of the lead is beneficial as it assists in retaining the lead in its implanted site.

Where the lead is a transvenous defibrillator lead for correcting ventricular tachycardia, the tissue stimulating electrode comprises a helically wound coil formed of uninsulated wire. After implantation of such a lead, there is extensive fibrotic tissue growth between the coil turns and around the shocking coils. Explanting such defibrillator leads is time consuming and carries potential surgical risk. In one embodiment a pliable sheath covers at least a portion of the shocking coils, thereby minimizing or eliminating direct contact of the shocking coil with the biological environment. The construction of the sheath is such that it can transfer electrical energy from the surface of the shocking coil. At least a portion of the outer surface of this sheath is adapted to stimulate cardiac tissue, by being inherently conductive, without relying on porosity and body fluid for charge transfer.

DETAILED DESCRIPTION

In the following detailed description of the preferred embodiments, reference is made to the accompanying drawings which form a part hereof wherein like numerals designate like parts throughout, and in which is shown by way of illustration specific embodiments in which the invention may be practiced. It is to be understood that other embodiments may be utilized and structural or logical changes may be made without departing from the scope of the present invention. Therefore, the following detailed description is not to be taken in a limiting sense, and the scope of the present invention is defined by the appended claims and their equivalents.

Figure 1:
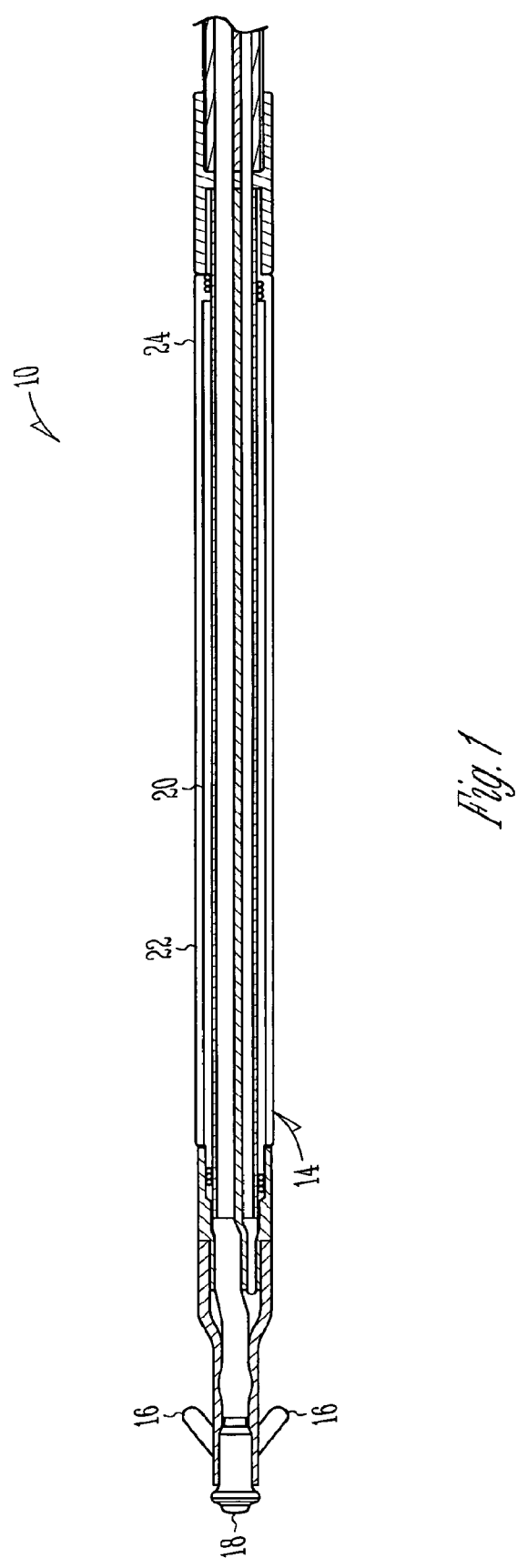
FIG. 1 is an axial cross section view of the distal electrode of an implantable endocardial lead in accordance with the present invention.

FIG. 1 shows a portion of an implantable endocardial lead, referred to generally at 10, in accordance with one embodiment of the present invention. The present invention contemplates any lead configuration known in the art, especially a suitable defibrillator lead configuration having a proximal end, a distal end and at least one electrode at its distal end. FIG. 1 shows a distal electrode 14 located at the distal portion 12 of the lead 10. The distal portion 12 of the lead 10 has a fixation mechanism 16 which anchors the distal end of the lead 10, and a distal tip electrode 18. Distal electrode 14 comprises an uninsulated, helically wound shocking coil 20, covered by a pliable, electrically conductive sheath 22.

A flexible tubular sheath 22 covers outer surface 24 of shocking coil 20. Sheath 22 covers at least a portion of the shocking coil 20. Sheath 22 is electrically conductive. Sheath 22 is constructed and arranged to minimize adhesion and tissue ingrowth while passing sufficient electrical energy to stimulate the cardiac tissue. The thickness of the sheath is from about 0.0005 to about 0.010 inch. In a preferred embodiment, the thickness of the sheath is from about 0.001 to about 0.005 inch.

In one embodiment, sheath 22 may be made of a nonporous material which is electrically conductive. In another embodiment, sheath 22 may be made of a porous electrically conductive material, although the conductivity of the sheath 22 is not dependent on the porosity of the material.

The conductivity of the sheath is expressed as volume resistivity. The sheath has a volume resistivity in the range of from about 0.0001 ohm-cm to about 0.50 ohm-cm. In a preferred embodiment, the volume resistivity is from about 0.0001 ohm-cm to about 0.10 ohm-cm. Sheath 22 according to the present invention may be affixed to shocking coil 20 by common methods known in the art.

Figure 2:
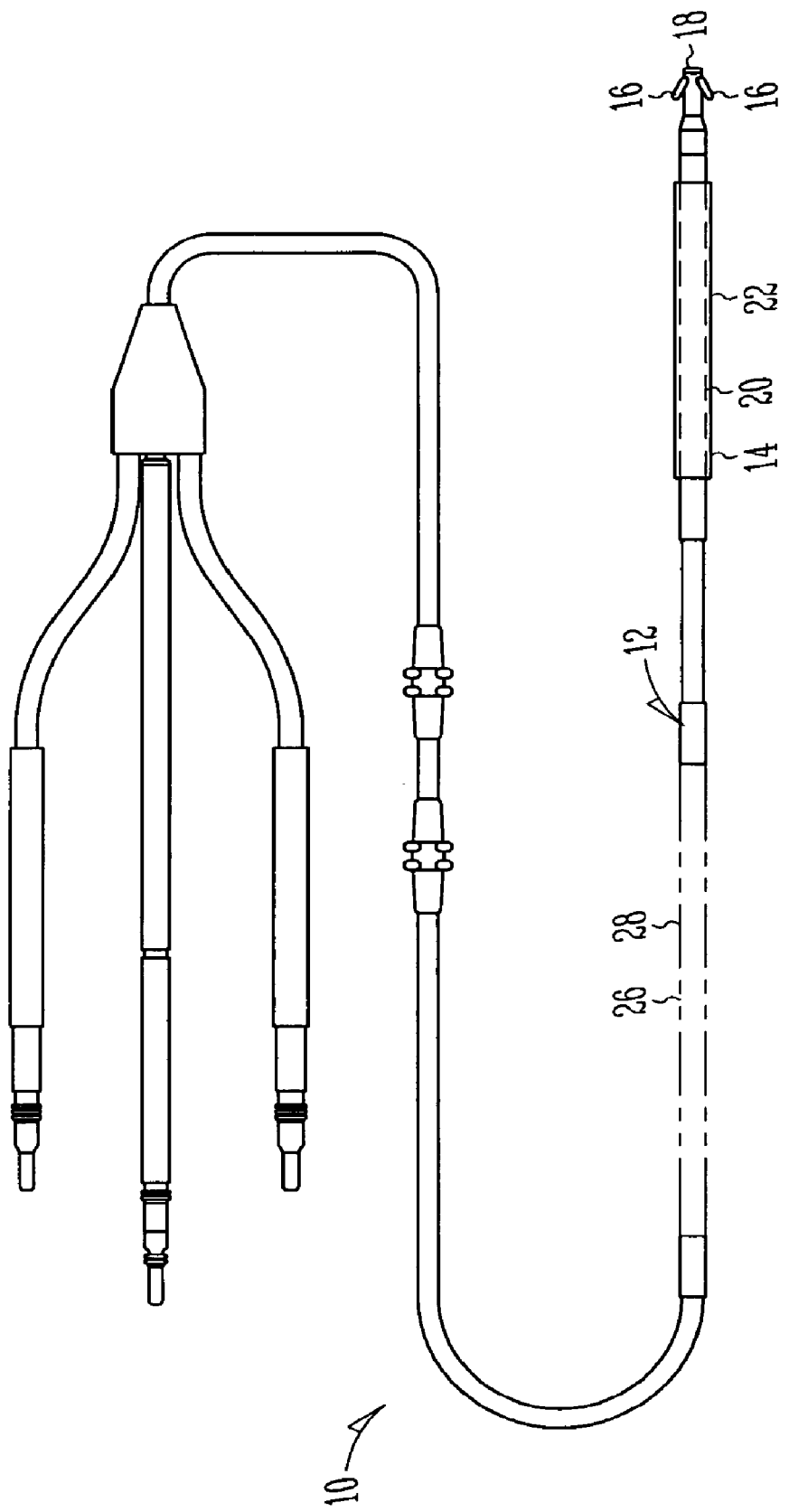
FIG. 2 is a side view of a lead according to one embodiment of the present invention.
Figure 3:
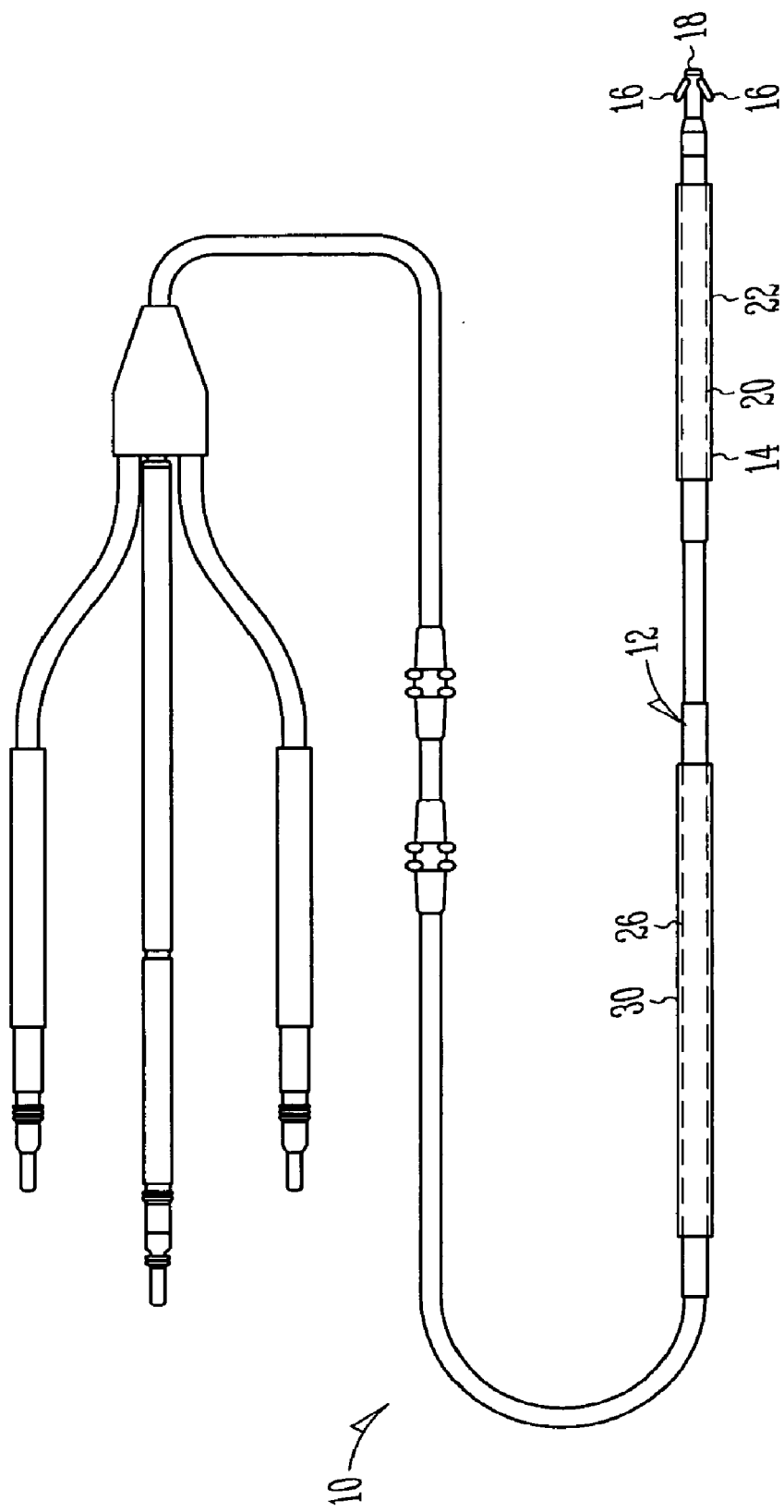
FIG. 3 is a side view of a lead according to one embodiment of the present invention.
Figure 4:
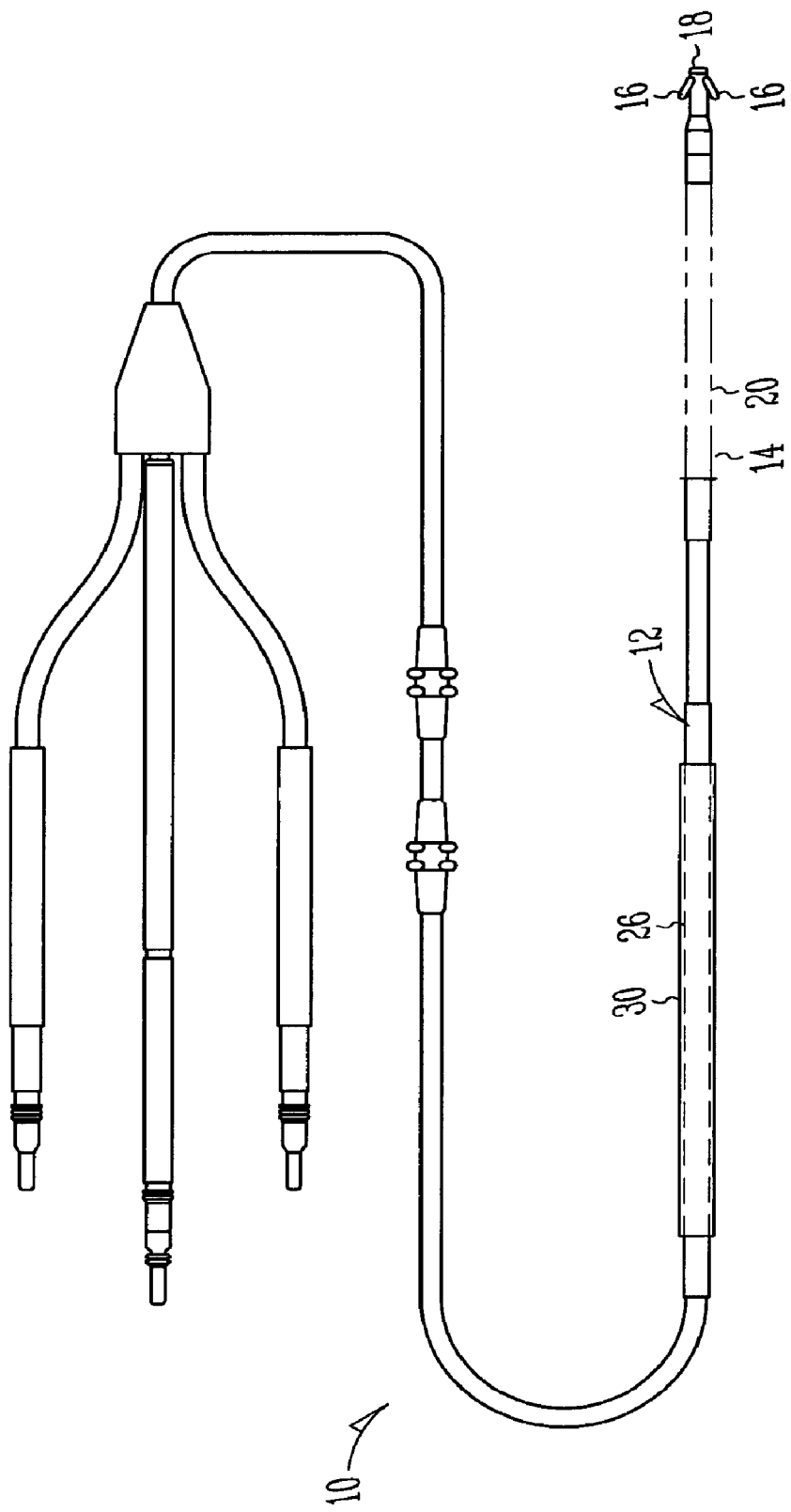
FIG. 4 is a side view of a lead according to one embodiment of the present invention.

In one embodiment, the distal portion of lead 10 includes a second electrode. Referring to FIG. 2, proximal electrode 26 comprises an uninsulated, helically wound shocking coil 28. In a further embodiment, at least a portion of proximal electrode 26 is covered by a pliable electrically conductive sheath 30. Lead 10 may optionally be provided having the proximal electrode 26 covered by sheath 30 and the distal electrode 14 being uncovered as shown in FIG. 4. Alternatively, lead 10 may be provided having the proximal electrode uncovered and the distal electrode 14 covered by sheath 22 as shown in FIG. 2. In one embodiment, lead 10 may be provided with the proximal electrode 26 covered by sheath 30 and the distal electrode covered by sheath 22 as shown in FIG. 3.

In one embodiment, lead 10 further comprises a distal tip electrode 18. Distal tip electrode is porous, and may be made of a metallic mesh.

Lead 10 according to the present invention includes a fixation mechanism 16 which anchors the distal end thereof. While fibrosis at the site of the distal tip of the lead is beneficial in that it assists in retaining the lead in its implanted site, fibrosis at the shocking coils is problematic. Explanting defibrillator leads is time-consuming and carries potential surgical risk due to the extensive tissue ingrowth or fibrosis that occurs between and around shocking coils.

The present invention minimizes or eliminates this problem by the use of a pliable, electrically conductive sheath around the shocking coil. The construction of the sheath is such that it can transfer electrical energy from the surface of the underlying coil to the cardiac tissue it is in contact with. At least a portion of the outer surface of this sheath is adapted to stimulate cardiac tissue, by being inherently electrically conductive, without relying on porosity and body fluid for charge transfer.

Sheath 22 provides shocking coil 20 with an electrically conductive surface exposed to blood, such that tissue ingrowth is minimized and passage of electrical energy is not compromised.

Sheath 22 is made of a flexible polymeric material. This polymeric material is non-biodegradable and biocompatible, and serves as the substrate for providing an electrically conductive path by way of either any suitable electrically conductive coatings deposited on the polymer surface, or any suitable electrically conductive particles blended with the polymer, prior to converting it to the final form. It is evident that in all these variants, the electrical conductivity is a fundamental material characteristic and not based on porosity.

Examples of the substrate polymers include but are not limited to silicone rubber, polyurethane, and homopolymers or copolymers of polyolefin, fluoropolymer, polyamide and polyester.

Examples of electrically conductive coatings on these polymers include but are not limited to coatings based on platinum, palladium, iridium, cobalt, silver, nickel and combinations thereof. Such coatings may be deposited by any methods commonly used in the industry, such as electroless deposition, plasma deposition, sputtering or chemical vapor deposition. The thickness of the coating is from about 0.0005 to about 0.005 inch. In a preferred embodiment, the thickness of the coating is from about 0.0005 to about 0.002 inch.

In one embodiment, the sheath is made of a polymer substrate of polyester, polyolefin or polyurethane, and has an electrically conductive coating of platinum. In a further embodiment the sheath is made of a polymer substrate selected from the group consisting of polyethylene terephthalate, polyethylene, polyether urethane and polysiloxane urethane, and has an electrically conductive coating of platinum.

In one embodiment, the sheath is made of a porous tube made of polyester, polyolefin or polyurethane, with an electrically conductive coating of platinum. In a further embodiment, the porous tube is made of a material selected from the group consisting of polyethylene terephthalate, polyethylene, polyether urethane and polysiloxane urethane, and has an electrically conductive coating of platinum.

Examples of electrically conductive particles that can be blended with the substrate polymer include but are not limited to various forms of carbon, stainless steel, nickel, silver, titanium, platinum and combinations thereof. For example, in one embodiment the sheath is made of silicone rubber blended with particles of glassy carbon.

Conductivity of the sheath provides an electrical interface between the coil and the tissue, the inner diameter of the sheath contacting the coil and the outer diameter of the sheath contacting the tissue.

The sheath may be provided in the form of an extruded tube, a molded tube, a braided tube, a woven tube, a knitted tube or a tubular structure made by any method commonly known in the art.

Any suitable materials known in the art that would enable the design of the inventive lead are also within the scope of the present invention.

The present invention is advantageous over prior art devices that are based on porosity. Such devices function by passage of electrical conductivity via porosity in the surface contacting the cardiac tissue and the resulting contact with bodily fluid. The porous materials of choice outlined in the prior art devices suffer from various drawbacks, including ineffective electrical charge transfer, manufacturing challenges in lead assembly, poor bonding characteristics, the need to be wetted by body fluids, poor wetting characteristics, the need to add a surface wetting agent, biocompatibility and biostability issues, and in the case of hydrogel, moisture sensitivity during manufacture.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiment shown and described without departing from the scope of the present invention. Those with skill in the biotechnology and medical device arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A lead comprising:
   a proximal portion;
   a distal portion comprising a first tissue-stimulating electrode having an outer surface and an inner surface, at least a portion of the outer surface of the first electrode being adapted to stimulate cardiac tissue; and
   a first flexible tubular sheath having an outer surface and an inner surface disposed over and in contact with at least a portion of the outer surface of the first tissue-stimulating electrode, the first sheath comprising polysiloxane urethane or polyether urethane and a conductive material, the first sheath being adapted to minimize adhesion and tissue ingrowth while passing sufficient electrical current to stimulate cardiac tissue when the lead is implanted in, on or about a heart.

2. The lead according to claim 1, wherein the first flexible, tubular sheath is non-porous.

3. The lead according to claim 1, wherein the conductive material comprises particles selected from the group consisting of carbon, stainless steel, nickel, silver, titanium, platinum or combinations thereof.

4. The lead according to claim 1, wherein the conductive material comprises platinum particles.

5. The lead according to claim 1, wherein the conductive material comprises glassy carbon particles.

6. The lead according to claim 1, wherein the first flexible, tubular sheath further includes a conductive coating on the outer and inner surfaces of the sheath, the conductive coating comprising the conductive material.

7. The lead according to claim 6, wherein the conductive material is selected from the group consisting of platinum, palladium, iridium, cobalt, silver, nickel or combinations thereof.

8. The lead according to claim 6, wherein the conductive material comprises platinum.

9. The lead according to claim 1, wherein the conductive material comprises conductive particles and is blended with the polymer substrate.

10. The lead according to claim 1, wherein the first flexible, tubular sheath has a thickness in a range from about 0.0005-0.010".

11. The lead according to claim 10, wherein the first flexible, tubular sheath has a thickness in a range of about 0.001-0.005".

12. The lead according to claim 1, wherein the first flexible, tubular sheath has a volume resistivity in a range of about 0.0001-0.50 ohm-cm.

13. The lead according to claim 12, wherein the first flexible, tubular sheath has a volume resistivity in a range of about 0.0001-0.1 ohm-cm.

14. The lead according to claim 1, further comprising a second tissue-stimulating electrode spaced apart from the first electrode along a longitudinal axis of the lead, and a second flexible tubular sheath comprising a polymer and a conductive material having an outer surface and an inner surface disposed over and in contact with at least a portion of the outer surface of the second electrode, the second sheath being adapted to minimize adhesion and tissue ingrowth while passing sufficient electrical current to stimulate cardiac tissue when the lead is implanted in, on or about a heart.

15. The lead according to claim 1, wherein:
the first electrode is a defibrillation shocking coil electrode; and
the first flexible, tubular sheath is disposed over and in contact with the entire outer surface of the first electrode.

16. The lead according to claim 1, wherein the first sheath comprises polyether urethane.

17. The lead according to claim 1, wherein the first sheath comprises polysiloxane urethane.

* * * * *